US012153062B2

(12) United States Patent
Hozumi

(10) Patent No.: US 12,153,062 B2
(45) Date of Patent: Nov. 26, 2024

(54) METHOD FOR ESTIMATING PHYSICAL PROPERTY OF AQUEOUS SAMPLE

(71) Applicant: Kao Corporation, Tokyo (JP)

(72) Inventor: Kenji Hozumi, Wakayama (JP)

(73) Assignee: KAO CORPORATION, Tokyo (JP)

(*) Notice: Subject to any disclaimer, the term of this patent is extended or adjusted under 35 U.S.C. 154(b) by 920 days.

(21) Appl. No.: 17/268,404

(22) PCT Filed: Aug. 26, 2019

(86) PCT No.: PCT/JP2019/033207
§ 371 (c)(1),
(2) Date: Feb. 12, 2021

(87) PCT Pub. No.: WO2020/045321
PCT Pub. Date: Mar. 5, 2020

(65) Prior Publication Data
US 2021/0208042 A1 Jul. 8, 2021

(30) Foreign Application Priority Data
Aug. 31, 2018 (JP) .............................. JP2018-163916

(51) Int. Cl.
G01N 1/00 (2006.01)
C11D 1/00 (2006.01)
C11D 1/72 (2006.01)
C11D 1/83 (2006.01)
C11D 3/18 (2006.01)
C11D 3/20 (2006.01)
G01N 1/10 (2006.01)
G01N 5/04 (2006.01)
G01N 33/00 (2006.01)

(52) U.S. Cl.
CPC ................. *G01N 5/04* (2013.01); *C11D 1/83* (2013.01); *G01N 1/10* (2013.01)

(58) Field of Classification Search
CPC .. G01N 1/00; G01N 1/10; G01N 5/04; G01N 33/00; C11D 1/00; C11D 1/72; C11D 3/18; C11D 3/20; C11D 3/2068; C11D 3/2093
See application file for complete search history.

(56) References Cited

U.S. PATENT DOCUMENTS

2015/0275627 A1* 10/2015 Xu ..................... G01N 33/1826
436/30

FOREIGN PATENT DOCUMENTS

| JP | 63-65345 A | 3/1988 |
| JP | 2009-148190 A | 7/2009 |
| JP | 2015-152322 A | 8/2015 |

OTHER PUBLICATIONS

Johansson et al, "About Characterization of Surfactants Outside the HLB-System", CD Proceedings 6th World Surfactant Congress CESIO, Berlin Germany, Paper #65, pp. 1-12, Jun. 21-23, 2004.*
International Search Report for PCT/JP2019/033207 (PCT/ISA/210) mailed on Nov. 19, 2019.
Mizutani, "The Correlation between the Temperature of Phase Inversion and the Cloud Point or HLB Value in Emulsion by Nonionic Emulsifier", Nippon kagaku zassi, 1966, vol. 87, No. 8, pp. 818-821.
Yamashita et al., "Novel Indexation to Express Interfacial Properties of Surface Active Materials", The University Bulletin of Chiba Institute of Science, 2013, vol. 6, pp. 89-92.
Fukuda et al., "Importance of the Lipophobicity of Hydrophilic Groups of Surfactants and Evaluation," Journal of Japan Oil Chemists' Society, vol. 48, No. 6, 1999, pp. 45-52 (11 pages total) with partial English translation.
International Preliminary Report on Patentability and English translation of the Written Opinion of the International Searching Authority for International Application No. PCT/JP2019/033207, dated Mar. 2, 2021.
Kitahara et al. (ed.), "Surfactant: Properties, Applications and Chemical Ecology," 7th printing, Kodansha Ltd., May 1990, pp. 24-25, 565 (4 pages total) with partial English translation.
Kunieda et al., "The Effect of Temperature on the Solution Behavior of Hydrophole-Lipophile-Balanced Ionic Surfactant," Oil Chemistry, Japan Oil Chemists' Society, vol. 29, No. 7, 1980, pp. 70-73, with English abstract.
Mizutani, "The Correlation between the Temperature of Phase Inversion and the Cloud Point or HLB Value in Emulsion by Nonionic Emulsifier", Nippon kagaku zassi 1966 vol. 87 No. 8 pp. 818-821 with English abstract.
Nishi (ed.) et al., "Handbook of Surfactants," 8th Printing, Nov. 30, 1969, pp. 307-309, 318-320 (14 pages total) with partial English translation.
Shinoda et al., "Comparison of Emulsifier Selections by Phase Inversion Temperature Method and HLB Value Method," Journal of the Chemical Society of Japan, vol. 89, No. 5, 1968, pp. 435-442 (9 pages total), with English abstract.
Yamashita et al., "Novel Indexation to Express Interfacial Properties of Surface Active Materials", The University Bulletin of Chiba Institute of Science, 2013, vol. 6, pp. 89-92, with English abstract.
Extended European Search Report dated May 24, 2022 for Application No. 19853466.1.
Horiuchi, "Basic Theory of Emulsification", J. Soc. Cosmet. Chem. Jpn., vol. 44, No. 1, 2010, pp. 2-22, with an English abstract.
Japanese Office Action dated May 31, 2022, for Application No. 2018-163916.

(Continued)

*Primary Examiner* — Brian P Mruk
(74) *Attorney, Agent, or Firm* — Birch, Stewart, Kolasch & Birch, LLP

(57) ABSTRACT

The present invention is a method for estimating a physical property of an aqueous sample containing a surfactant and water, comprising: adding an oil component and a phase-changing probe to the aqueous sample, and estimating the physical property of the aqueous sample from an amount of the phase-changing probe when a phase structure of the mixture changes.

9 Claims, 6 Drawing Sheets

(56) References Cited

OTHER PUBLICATIONS

Johansson et al., "About Characterization of Surfactants Outside the HLB-System", CD Proceedings 6th World Surfactant Congress CESIO, Berlin Germany, Jun. 21-23, 2004. (paper # 65). 12 pages.
Miller et al., "Phase inversion of W/O emulsions by adding hydrophilic surfactant—a technique for making cosmetics products", Colloids and Surfaces A: Physicochemical and Engineering Aspects, vol. 183-185, 2001, pp. 681-688.
Najjar et al. "Modified diesel prepared by stabilization of water as nanodroplets in diesel/colza oil blend: Study of phase behavior and affecting parameters", Fuel, vol. 214, 2018 (Available online Nov. 22, 2017), pp. 497-504.
Verdinelli et al., "Hydrophile-lipophile balance (HLB) of n-alkane phosphonic acids and theirs salts", Colloids and Surfaces A: Physicochem. Eng. Aspects, vol. 316, 2008 (Available online Aug. 30, 2007), pp. 131-135.

* cited by examiner

<Graph I>

METHOD FOR ESTIMATING PHYSICAL PROPERTY OF AQUEOUS SAMPLE

FIELD OF THE INVENTION

The present invention relates to a method for estimating a physical property of an aqueous sample.

BACKGROUND OF THE INVENTION

Compositions containing surfactants have been widely applied to washing or emulsification technologies or the like. In addition, as a yardstick for measuring the detergency or emulsifying ability of surfactants, HLB (hydrophilic-lipophilic balance) has been commonly used as an indicator. While such HLB is represented by a numerical value of Griffin's method, Davies' method or the like, Griffin's method is intended mainly for nonionic surfactants and Davies' method has been known to be not very practical for lack of basic data (*Kaimenkasseizai: Bussei•Ōy ō•Kagaku-seitai-gaku*, edited by Fumio KITAHARA, May 1990, 7th printing, Kodansha Ltd.). Thus, these HLB values are difficult to apply to anionic, cationic or amphoteric surfactants and further difficult to apply to compositions containing a plurality of types of surfactants from among them. Further, while in general, for the purpose of improving stability, detergency or the like, various additives such as solvents, salts or the like other than surfactants are used in compositions depending on their purposes, in such compositions, HLB values of the surfactants alone are difficult to serve as an indicator for composition design, and thus, in order to obtain a desired liquid physical property, trial and error are inevitable. Hence, estimating a physical property of a complex liquid composition containing a plurality of types of surfactants and additives such as salts, solvents or the like is very useful for composition design.

While JP-A 2015-152322 discloses a technique of creating a function with partition coefficients determined respectively from normal-phase chromatography and reversed-phase chromatography and using it as a yardstick for measuring hydrophilicity and hydrophobicity, it is a technique used only for polyhydric alcohol-based surfactants.

Morinobu FUKUDA and Kozo SHINODA, "Importance of the Lipophobicity of Hydrophilic Groups of Surfactants and Evaluation," Journal of Japan Oil Chemists' Society, Japan Oil Chemists' Society, Volume 48, No. 6 (1999), pages 45-52 describes a method for estimating a dissolved state of a surfactant by quantifying a structuralized component with high-speed liquid chromatography.

Hironobu KUNIEDA, "The Effect of Temperature on the Solution Behavior of Hydrophile-Lipophile-Balanced Ionic Surfactant," Oil Chemistry, Japan Oil Chemists' Society, Volume 29, No. 7 (1980), pages 70-73 describes effects of temperature on a dissolved state of a hydrophile-lipophile-balanced ionic surfactant.

KöZö SHINODA, "Comparison of Emulsifying Agent Selection between Phase-change Temperature Method and HLB Value Method," Journal of the Chemical Society of Japan, the Chemical Society of Japan, Volume 89, No. 5 (1968), pages 435-442 describes a method for inferring a state of a system from a relation between a phase-change temperature and a surfactant.

SUMMARY OF THE INVENTION

However, the approaches of these patent and non-patent documents cannot estimate a physical property of a complex liquid composition containing a plurality of types of surfactants and additives such as salts, solvents or the like.

The present invention provides a method for estimating, by a simple measuring method, a physical property, for example, hydrophobicity, of an aqueous composition including a surfactant and water, for example, a complex liquid composition containing a plurality of types of surfactants and additives such as salts, solvents or the like.

The present invention relates to a method for estimating a physical property of an aqueous sample containing a surfactant and water, including:
  adding an oil component and a phase-changing probe to the aqueous sample, and estimating the physical property of the aqueous sample from an amount of the phase-changing probe when a phase structure of the mixture changes.

Examples of the method of the present invention include a method for estimating a physical property of an aqueous sample containing a predetermined concentration of surfactant and water, including:
  preparing a standard sample by adding an oil component and optionally a solvent to a precursor sample containing water and a surfactant with a known Griffin's HLB value, the concentration of the surfactant with a known Griffin's HLB value being the same as the concentration of the surfactant in the aqueous sample; adding to the standard sample a phase-changing probe composed of a compound having a different structure than that of the surfactant with a known Griffin's HLB value to quantify an amount of the phase-changing probe required until a phase structure of the standard sample changes; performing this quantification for a plurality of surfactants with different Griffin's HLB values under the same conditions to obtain a plurality of quantitative values; and preparing a calibration curve from the quantitative values and the HLB values of the surfactants included in the standard samples that provide the quantitative values,
  preparing a measurement sample by adding to the aqueous sample the same oil component and optional solvent as those added to the precursor sample in the same respective amounts as those in the precursor sample; adding to the measurement sample the same phase-changing probe as the one used for the measurement of the quantitative values of the calibration curve; and quantifying an amount of the phase-changing probe required until a phase structure of the measurement sample changes, and
  with values of the HLB value in the calibration curve defined as liquid physical property indexes, estimating the physical property of the aqueous sample from a liquid physical property index corresponding to a quantitative value of the phase-changing probe for the measurement sample.

In addition, the present invention relates to a method for producing a liquid composition with a desired physical property containing a surfactant and water, including:
  estimating, by the aforementioned method of the present invention, a physical property of an aqueous composition containing a surfactant and water, the surfactant being at least one surfactant with which the final liquid composition is formulated; and
  in response to the estimated physical property, determining whether or not to change the composition of the aqueous composition.

In addition, the present invention relates to a method for adjusting a physical property of an aqueous composition, including:
estimating a physical property of an aqueous composition containing a surfactant and water by the aforementioned method of the present invention; and
in response to the estimated physical property, changing the composition of the aqueous composition to adjust the physical property of the aqueous composition.

In addition, the present invention relates to a method for preparing a calibration curve for estimating a physical property of an aqueous sample containing a predetermined concentration of surfactant and water from an amount of a phase-changing probe added to the aqueous sample, including:
preparing a standard sample by adding an oil component and optionally a solvent to a precursor sample containing water and a surfactant with a known Griffin's HLB value, the concentration of the surfactant with a known Griffin's HLB value being the same as the concentration of the surfactant in the aqueous sample;
adding to the standard sample the phase-changing probe composed of a compound having a different structure than that of the surfactant with a known Griffin's HLB value to quantify an amount of the phase-changing probe required until a phase structure of the standard sample changes, and performing this quantification for a plurality of surfactants with different Griffin's HLB values under the same conditions to obtain a plurality of quantitative values; and
preparing the calibration curve from the quantitative values and the HLB values of the surfactants included in the standard samples that provide the quantitative values.

In addition, the present invention relates to an apparatus for estimating a physical property of an aqueous sample containing a predetermined concentration of surfactant and water from an amount of a phase-changing probe added to the aqueous sample, including:
a measurement unit to measure an added amount of the phase-changing probe; an input unit to input the added amount of the phase-changing probe; a calibration curve acquisition unit to acquire a calibration curve from input measurement values; and a determination unit to determine a physical property of the aqueous sample by applying an added amount of the phase-changing probe to the calibration curve,
wherein the measurement unit includes: a container to contain the aqueous sample or a standard sample containing a surfactant with a known Griffin's HLB value, an oil component, water and optionally a solvent; a supply device to add to the aqueous sample or the standard sample the phase-changing probe composed of a compound having a different structure than that of the surfactant with a known Griffin's HLB value; and a recording device to record an added amount of the phase-changing probe required until a phase structure of the aqueous sample or the standard sample changes,
the measurement unit acquires a plurality of amounts (I) of the phase-changing probe added for a plurality of surfactants with different Griffin's HLB values under the same conditions, and added amounts (I) are input to the calibration curve acquisition unit as the measurement values to acquire the calibration curve, and
the determination unit includes a determination device to acquire, on the basis of added amount (II), received from the recording device, of the phase-changing probe required until a phase structure of the aqueous sample changes, a Griffin's HLB value corresponding to added amount (II) in the calibration curve.

In addition, the present invention relates to a calibration curve preparation kit for preparing a calibration curve for estimating a physical property of an aqueous sample containing a predetermined concentration of surfactant and water from an amount of a phase-changing probe added to the aqueous sample, including:
a plurality of standard samples each containing a surfactant with a known Griffin's HLB value, an oil component, water and optionally a solvent; and
a phase-changing probe composed of a compound having a different structure than that of the surfactant with a known Griffin's HLB value,
wherein the plurality of standard samples are of the same composition except that the Griffin's HLB values of the surfactants are different from one another, and
in each of the plurality of standard samples, the concentration of the surfactant with a known Griffin's HLB value in the total of the surfactant with a known Griffin's HLB value and water is the same as the concentration of the surfactant in the aqueous sample.

According to the present invention, provided is a method for estimating, by a simple measuring method, a physical property of an aqueous composition including a surfactant and water, for example, a complex liquid composition containing a plurality of types of surfactants and additives such as salts, solvents or the like.

While aqueous compositions containing surfactants and water have been widely applied in such industrial fields as, for example, detergent, cosmetics and the like, they are not such simple compositions as contain only surfactants and water, but generally include various inorganic or organic compounds as components which attain various purposes such as a medicinal component, a functional component, a solvent, a fragrance, a colorant and the like. At the time of designing aqueous compositions directed to various applications, functions such as detergency, emulsifying ability, dispersibility, stability and the like are required. However, there is a possibility that the required functions are not attained due to a liquid physical property being changed when additives, assistant components or the like are added to change the composition for the purpose of improving aqueous compositions, and a great deal of trial and error is needed to satisfy the required functions.

According to the present invention, a liquid physical property of a complex aqueous composition containing surfactants can be estimated by, for example, defining, as an indicator, an index corresponding to a liquid physical property of a composition composed of a surfactant with a known Griffin's HLB value and water. The result serves as an indicator for improving the aqueous composition, and therefore can be utilized as useful information for reduction in time for adjusting the composition, new liquid composition design or the like.

EMBODIMENTS OF THE INVENTION

Figure 1:
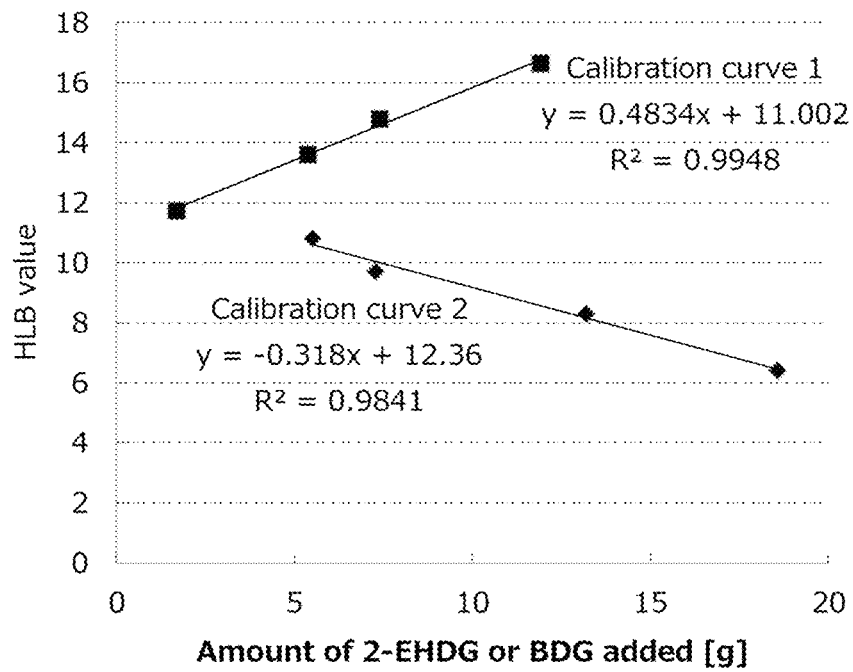
FIG. 1 shows Graph A containing calibration curves 1 and 2.
Figure 2:
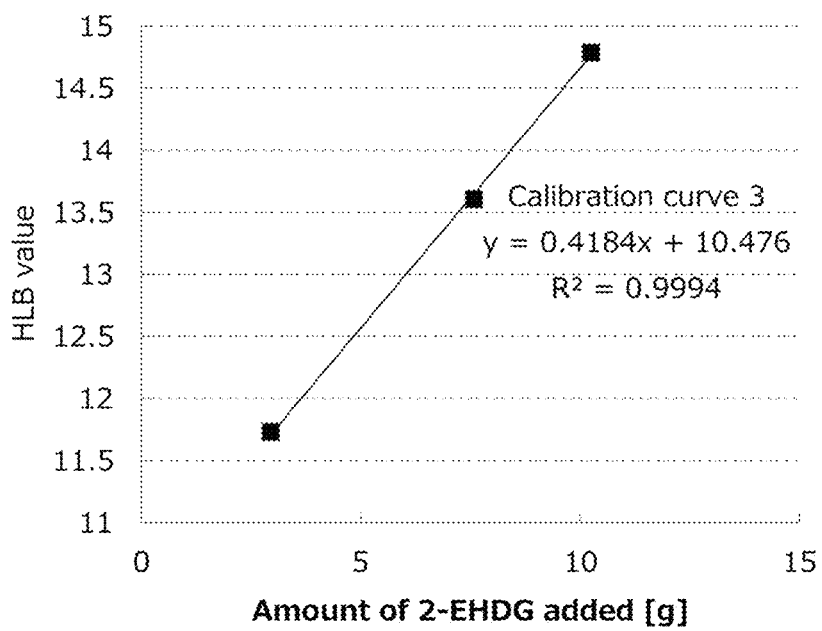
FIG. 2 shows Graph B containing calibration curve 3.
Figure 3:
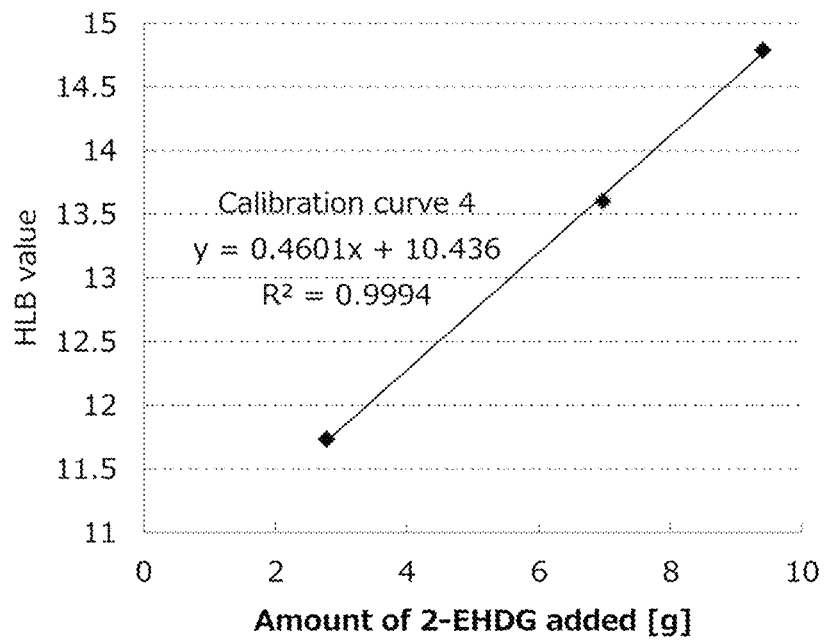
FIG. 3 shows Graph C containing calibration curve 4.
Figure 4:
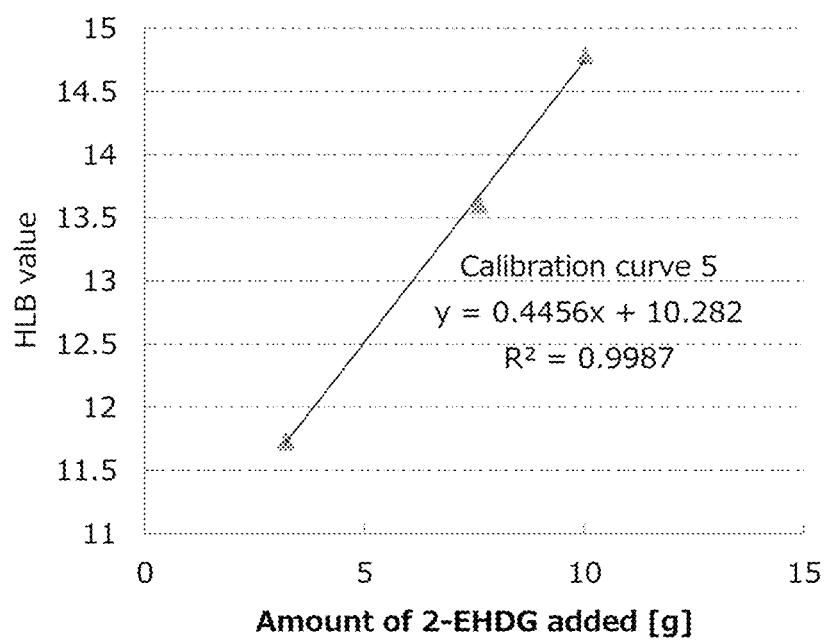
FIG. 4 shows Graph D containing calibration curve 5.
Figure 5:
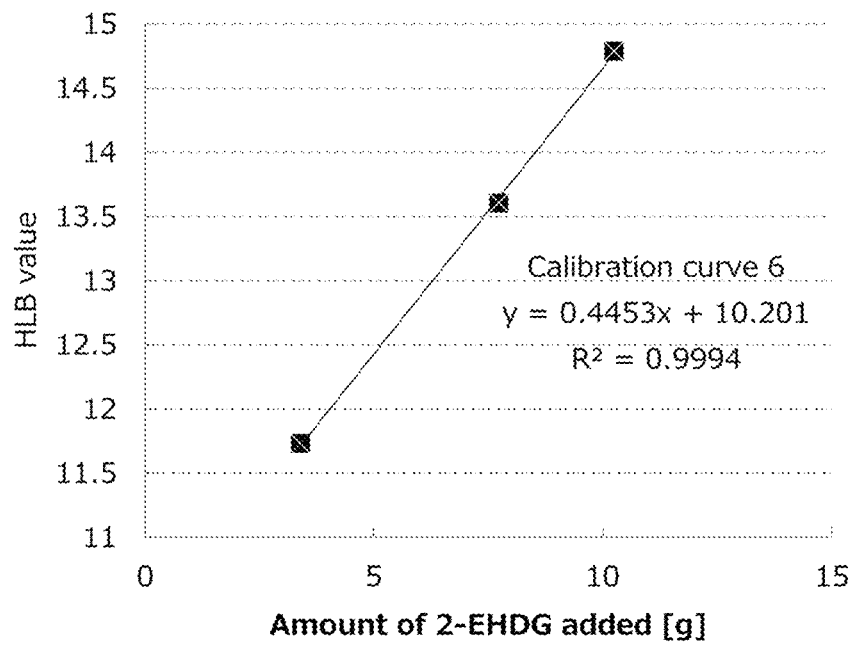
FIG. 5 shows Graph E containing calibration curve 6.
Figure 6:
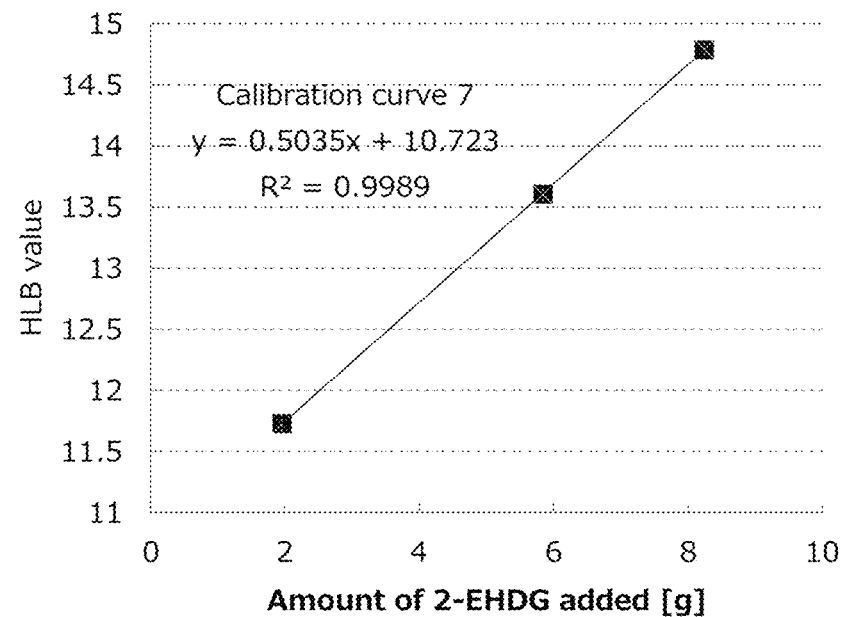
FIG. 6 shows Graph F containing calibration curve 7.

Compositions constituted of oil, water and surfactants have been known to change their phase structures due to changes in temperature, for example, from two phases of an oil phase (O phase) and a micellar solution phase (Wm phase) to two phases of a water phase (W phase) and a reversed micellar oil solution phase (Om phase). Particularly, as to systems in which nonionic surfactants are used, researches on phase structure changes are advancing and as a mechanism thereof, a change of a micellar or reversed micellar structure is understood as being caused by a transition to a thermodynamically-stable intermolecular structure due to an interaction between nonionic surfactants and water molecules, and a liquid physical property indicated by HLB can be envisaged. On the other hand, as to anionic or cationic surfactants or mixed systems of a plurality of surfactants, structure changes due to temperature changes are small and phase structure changes are also difficult to clearly observe, and further, in the case of anionic or cationic surfactants, a relation between a numerical value calculated as Griffin's or Davies' HLB and a phase structure change is ambiguous and a liquid physical property often cannot be properly determined. Then, the present inventors had studied the possibility of defining a state of a liquid physical property of an aqueous composition containing a nonionic surfactant whose HLB value is easy to calculate and has a high correlation with the liquid physical property as an indicator for a liquid physical property of an aqueous composition containing various surfactants such as nonionic, anionic or cationic surfactants, a mixed system of a plurality of surfactants or the like, and established a method for estimating the liquid physical property of the aqueous composition on the basis of a phase structure change caused by using a phase-changing probe, for example, estimating by using the index defined in the present invention as a yardstick.

While the entire working mechanism of the present invention is not wholly revealed, it is considered as follows.

A phase structure change in a mixed system constituted of oil (O phase), water (W phase) and a surfactant is considered as follows: in the case where this mixed system forms a certain phase structure, for example, in the case where it forms two phases (O+Wm) of O phase and a micellar solution phase (Wm phase) like in a micellar structure or the like, if a hydrophobic substance, for example, a hydrophobic surfactant or organic solvent which is different from the surfactant forming the phase (referred to as a phase-changing probe in the present invention) is added, the phase-changing probe is captured into a surfactant's membrane structure formed by the surfactant, thereby affecting the hydrophobic group moiety and changing a curvature of the membrane structure formed by the surfactant; as a result, a thermodynamically-stable system is changed from O+Wm to two phases (W+Om) of a water phase (W phase) and a reversed micellar oil solution phase (Om phase); and in reverse, in the case where it forms W+Om, if a hydrophilic phase-changing probe which is different from the surfactant forming the phase is added, the phase-changing probe is captured into a surfactant's membrane structure formed by the surfactant, thereby affecting the hydrophilic group moiety and changing a curvature of the membrane structure formed by the surfactant, and a thermodynamically-stable system is changed from Om+W to O+Wm. It has been found that, in such a phase structure change, the same behavior is observed whether in a nonionic surfactant, or an anionic or cationic surfactant or a mixed system of a plurality of surfactants. Then, in the case where a liquid physical property of an aqueous composition (aqueous sample) containing an unknown surfactant is estimated, a certain oil component is added to form a phase structure and a phase-changing probe is thereafter added to quantify an amount of the phase-changing probe required until it causes a phase structure change. A calibration curve is prepared in advance in such a manner that: a certain oil component is similarly added to a plurality of aqueous compositions (precursor samples) each containing a nonionic surfactant with a known Griffin's HLB value and water to form a phase structure; thereafter, the phase-changing probe is added; and the calibration curve is prepared from amounts of the phase-changing probe required until it causes a phase structure change and the HLB values of the nonionic surfactants used. On the basis of an amount of the phase-changing probe required for the aqueous composition containing an unknown surfactant, the corresponding nonionic surfactant HLB value is read from this calibration curve. The aqueous composition containing an unknown surfactant is considered to have the same liquid physical property as that of an aqueous composition including the nonionic surfactant with that HLB value. In the present invention, the liquid physical property can be estimated with the HLB values of nonionic surfactants defined as liquid physical property indexes. Note that, in the present invention, various conditions such as a surfactant concentration in an aqueous composition and the like are set as conditions that make the judgement of a phase structure change easy.

[Method for Estimating Physical Property of Aqueous Sample]

The present inventors have found that a physical property of an aqueous sample containing a surfactant and water can be estimated from an amount of a phase-changing probe added to the aqueous sample until a phase structure of the mixture of the aqueous sample and the phase-changing probe changes.

In the present invention, the physical property of the aqueous sample can be estimated from, for example, a liquid physical property index. Here, examples of the liquid physical property index include an HLB-axis value which can be read from a calibration curve prepared in the following manner from amounts of the phase-changing probe required for aqueous compositions to change a phase structure.

<Preparation of Calibration Curve>

To a precursor sample containing a surfactant with a known Griffin's HLB value and water, an oil component of the same type and amount as the one added to the aqueous sample is added to prepare a standard sample. The same phase-changing probe as the one added to the aqueous sample is added to the standard sample and an amount of the phase-changing probe is quantified when a phase structure of the standard sample changes. This quantification is performed for a plurality of surfactants with different Griffin's HLB values under the same conditions to obtain a plurality of quantitative values. At this time, the concentration of the surfactant with a known Griffin's HLB value in the precursor sample is the same as the concentration of the surfactant in the aqueous sample for which an amount of the phase-changing probe is measured, and compounds having different structures are used for the phase-changing probe agent and the surfactant with a known Griffin's HLB value. The calibration curve is prepared from the respective quantitative values and the HLB values of the surfactants included in the standard samples that provide the quantitative values.

It is preferable that the concentration of the surfactant with a known Griffin's HLB value in the precursor sample be the same as the concentration in the aqueous sample for which an amount of the phase-changing probe is measured. Note that, in the present invention, the concentration of the surfactant in the precursor sample may be considered as being the same as that of the surfactant in the aqueous sample if both concentrations can be judged comparable by a person skilled in the art. Thus, for example, in the case where the surfactant concentration in the aqueous sample is unknown, a concentration estimated by a known quantitative method for surfactant concentrations or the like may be adopted to judge the surfactant concentration in the precursor sample as being the same as the estimated concentration. While examples of the method for estimating the concentration of the surfactant can include, for example, a quantitative method using measurement equipment such as high-speed liquid chromatography, nuclear magnetic resonance spectroscopy or the like, a method for quantifying by extracting surfactants using solvents or the like, a weight measurement method by evaporation to dryness and the like, it is not particularly limited as long as it is a method known to a person skilled in the art. Further, in the case of an aqueous sample using a plurality of types of surfactants, the surfactants are considered to contribute to a physical property of the aqueous sample differently depending on their types or amounts. However, in the present invention, from the viewpoint of estimating the physical property as the aqueous sample, the total concentration of the surfactants can be used without particularly considering the composition of the constituent surfactants or like. When the concentration of a surfactant in the aqueous sample whose physical property is to be estimated is unknown, the concentration of the surfactant can be determined by those methods. Therefore, the method of the present invention may include, as necessary, a step of determining the concentration of a surfactant in the aqueous sample to be measured.

The method of the present invention is suitable as a method for estimating hydrophobicity of an aqueous sample. An example of the aqueous sample is an aqueous composition containing a surfactant and water.

More specific examples of the method of the present invention include a method for estimating a physical property of an aqueous sample containing a predetermined concentration of surfactant and water, including:

preparing a standard sample by adding an oil component and optionally a solvent to a precursor sample containing water and a surfactant with a known Griffin's HLB value, the concentration of the surfactant with a known Griffin's HLB value being the same as the concentration of the surfactant in the aqueous sample; adding to the standard sample a phase-changing probe composed of a compound having a different structure than that of the surfactant with a known Griffin's HLB value to quantify an amount of the phase-changing probe required until a phase structure of the standard sample changes; performing this quantification for a plurality of surfactants with different Griffin's HLB values under the same conditions to obtain a plurality of quantitative values; and preparing a calibration curve from the quantitative values and the HLB values of the surfactants included in the standard samples that provide the quantitative values, preparing a measurement sample by adding to the aqueous sample the same oil component and optional solvent as those added to the precursor sample in the same respective amounts as those in the precursor sample; adding to the measurement sample the same phase-changing probe as the one used for the measurement of the quantitative values of the calibration curve; and quantifying an amount of the phase-changing probe required until a phase structure of the measurement sample changes, and with values of the HLB value in the calibration curve defined as liquid physical property indexes, estimating the physical property of the aqueous sample from a liquid physical property index corresponding to a quantitative value of the phase-changing probe for the measurement sample.

In this method, the phase structure of the standard sample and/or measurement sample before adding the phase-changing probe may be a structure selected from an oil phase (O phase), a reversed micellar oil solution phase (Om phase), a bicontinuous phase (D phase), a micellar solution phase (Wm phase) and a water phase (W phase).

In the present invention, the amount of the phase-changing probe required until a phase structure changes is an amount of the phase-changing probe required until the phase structure of the standard sample and/or measurement sample before adding the phase-changing probe changes to any another phase structure. Further, in the case where a plurality of phase structure changes are caused by adding the phase-changing probe, the phase change which is easy to measure by visual observation or optical equipment can be arbitrarily selected.

In the present invention, examples of the phase structure change which is easy to distinguish for example by visual observation include a change from a micellar solution phase (Wm phase) to a composite phase of a reversed micellar oil solution phase (Om phase) and a water phase (W phase), as well as a change from a micellar solution phase (Wm phase) to a composite phase of a bicontinuous phase (D phase) and a water phase (W phase).

As the phase-changing probe, a compound having the function of changing a phase structure formed by a surfactant aqueous solution by forming a mixed micellar with the surfactant in water can be used.

Examples of the phase-changing probe include compounds having a hydrocarbon group with 2 or more and 20 or less carbons and a nonionic hydrophilic group. Examples of the nonionic hydrophilic group include a polyoxyalkylene group, a glyceryl group, a glycoside group and the like.

Examples of the phase-changing probe include an ether compound having a hydrocarbon group with 2 or more and 20 or less carbons and a polyoxyalkylene group whose average number of added moles is 1 or more and 10 or less, preferably 1 or more and 5 or less and more preferably 1 or more and 3 from the viewpoint of enabling the clear judgement on the phase structure change. Here, the alkylene group of the polyoxyalkylene group has 2 and/or 3 carbons. The hydrocarbon group has preferably 3 or more, and preferably 12 or less and more preferably 9 or less carbons from the viewpoint of enabling the clear judgement on the phase structure change. In addition, examples of the hydrocarbon group include an alkyl group and an aryl group. The number of the hydrocarbon group which the ether compound has is preferably 1 or 2. In addition, examples of the phase-changing probe include an ester of a fatty acid with 8 or more and 20 or less carbons and a sugar or an alkylene oxide adduct thereof. Examples of the sugar include monosaccharides, disaccharides or oligosaccharides, and sorbitan and sucrose are preferable. Examples of the alkylene oxide include ethylene oxides.

The phase-changing probe is preferably a compound represented by the following general formula (1):

$$R^1-O-(AO)_n-R^2 \quad (1)$$

wherein $R^1$ is a hydrocarbon group with 2 or more and 20 or less carbons; $R^2$ is a hydrogen atom or a hydrocarbon group with 1 or more and 20 or less carbons; A is an alkylene group with 2 or more and 3 or less carbons; and n is a number of 0 or more and 10 or less when $R^2$ is a hydrogen atom and a number of 1 or more and 10 or less when $R^2$ is a hydrocarbon group.

$R^1$ is preferably an alkyl group from the viewpoint of enabling the clear judgement on the phase structure change. $R^1$ has preferably 3 or more and more preferably 4 or more, and preferably 12 or less and more preferably 9 or less carbons from the viewpoint of enabling the clear judgement on the phase structure change.

$R^2$ is preferably a hydrogen atom. When $R^2$ is a hydrocarbon group, an alkyl group is preferable. When $R^2$ is a hydrocarbon group, it has preferably 1 or more and more preferably 2 or more carbons from the viewpoint of enabling the clear judgement on the phase structure change, and preferably 12 or less and more preferably 8 or less carbons from the same viewpoint.

$R^1$ and $R^2$ have preferably 4 or more carbons in total.

A is preferably an alkylene group with 2 carbons, that is, an ethylene group.

n is an average number of added moles.

when $R^2$ is a hydrogen atom, n is a number of preferably 1 or more, and preferably 5 or less and more preferably 3 or less from the viewpoint of enabling the clear judgement on the phase structure change.

when $R^2$ is a hydrocarbon group, n is a number of preferably 2 or more, more preferably 3 or more and further preferably 4 or more, and preferably 8 or less.

More specific examples of the phase-changing probe include compounds selected from polyoxyethylene alkyl ether, polyoxypropylene alkyl ether, monoalkyl monoglyceryl ether, alkyl polyglyceryl ether, polyalkyl glycoside, polyoxyalkylene alkylamine, polyoxyalkylene fatty acid ethanol amide and polyoxyethylene sorbitan alkyl ester. The alkyl groups of these compounds have preferably 3 or more and more preferably 4 or more, and preferably 10 or less and more preferably 8 or less carbons from the viewpoint of enabling the clear judgement on the phase structure change. As polyoxyethylene alkyl ether or polyoxypropylene alkyl ether, the compound of the aforementioned general formula (1) is preferable.

In the preparation of the calibration curve, a surfactant with a known Griffin's HLB value (hereinafter, sometimes also referred to as surfactant (G)) is used. Examples of surfactant (G) include nonionic surfactants described in Kaimenkasseizai Binran (Nov. 30, 1969, 8th printing, editors: Ichirō NISHI, Ichirō IMAI and Masatake KASAI, Publisher: Sangyo Tosho Publishing Co., Ltd.), pages 36 to 46. More specific examples thereof include nonionic surfactants selected from polyoxyalkylene alkyl ether, polyoxyalkylene alkylaryl ether, polyoxyalkylene alkyl thioether, polyoxyalkylene alkylaryl thioether, polyoxyalkylene alkyl ester, polyoxyalkylene sorbitan monoalkyl ester, polyoxyalkylene alkylamine, polyoxyalkylene alkyl amide, sorbitan alkyl ester, alkyl glyceryl ether, saccharide ester and fatty acid ethanol amide.

Examples of surfactant (G) include preferably a polyoxyethylene alkyl ether having an alkyl group with 8 or more and 18 or less carbons.

Examples of surfactant (G) include more preferably a compound represented by the following general formula (2):

$$R^3-O-(BO)_m-H \quad (2)$$

wherein $R^3$ is a hydrocarbon group with 10 or more and 20 or less carbons; B is an alkylene group with 2 or more and 3 or less carbons; and m is a number of 1 or more and 50 or less.

$R^3$ is preferably an alkyl group from the viewpoint of enabling the clear judgement on the phase structure change. $R^3$ has preferably 18 or less and more preferably 14 or less carbons from the viewpoint of enabling the clear judgement on the phase structure change.

B is preferably an alkylene group with 2 carbons, that is, an ethylene group.

m is an average number of added moles and a number of preferably 2 or more, and preferably 30 or less, more preferably 25 or less and further preferably 21 or less from the viewpoint of enabling the clear judgement on the phase structure change.

Note that, in the present invention, compounds having different structures are used for the phase-changing probe agent and surfactant (G). That is, for example, when the compound represented by the aforementioned general formula (1) is used as the phase-changing probe agent and the compound represented by the aforementioned general formula (2) is used as surfactant (G), it is considered that compounds having different structures are used respectively for them.

From the viewpoint of causing the phase structure change more quickly, it is preferable that the hydrocarbon group of the phase-changing probe have a smaller number of carbons than the hydrophobic group included in surfactant (G), e.g., the hydrocarbon group, has. Specifically, when the compound represented by the aforementioned general formula (1) is used as the phase-changing probe agent and the compound represented by the aforementioned general formula (2) is used as surfactant (G), the number of carbons of $R^1$ in the general formula (1) is preferably 2 or more and further 4 or more smaller than that of $R^3$ in the general formula (2).

A Griffin's HLB value of surfactant (G) is determined by a calculation method described in Kaimenkasseizai Binran (Nov. 30, 1969, 8th printing, editors: Ichirō NISHI, Ichirō IMAI and Masatake KASAI, Publisher: Sangyo Tosho Publishing Co., Ltd.), pages 307 to 309.

Note that a Griffin's HLB value is determined by the following formula in the case of a polyoxyalkylene-type nonionic surfactant:

HLB value=20×($M_H$/M) [$M_H$: molecular weight of hydrophilic group moiety, M: molecular weight]

When the numbers of added moles of the oxyalkylene group of the polyoxyalkylene group as the hydrophilic group moiety have a distribution, a molecular weight of the hydrophilic group moiety is determined by using an average value of the numbers of added moles.

In addition, it is determined by the following formula in the case of an ester-type nonionic surfactant:

HLB value=20×(1−S/A) [S: saponification value of ester, A: acid value of fatty acid]

Note that, as to a nonionic surfactant for which an HLB value cannot be determined by Griffin's method, a value determined by experiment is adopted as the HLB value. As the experimental method, a method described in *Kaimen-kasseizai Binran* (Nov. 30, 1969, 8th printing, editors: Ichirō NISHI, Ichirō IMAI and Masatake KASAI, Publisher: Sangyo Tosho Publishing Co., Ltd.), pages 318 to 320 is adopted.

For the preparation of the calibration curve, the oil component is used. The oil component is preferably a compound which is a liquid at 25° C. and which is dissolved in a micellar of surfactant (G). Examples of such a compound include a compound selected from hydrocarbons, ethers and esters, the compound having a solubility in water of 1 g/100 g or less at 25° C. and being liquid at 25° C.

Examples of the aforementioned hydrocarbons include a hydrocarbon with 4 or more, preferably 6 or more and more preferably 10 or more carbons from the viewpoint of enabling the clear judgement on the phase structure change, and 24 or less, preferably 20 or less and more preferably 18 or less carbons from the same viewpoint. More specific examples thereof include an isoparaffin with 16 carbons on average, hexadecane, tetradecane, dodecane, decane, hexane, cyclohexane and the like.

Examples of the aforementioned ethers include a compound with 6 or more and 20 or less carbons in total and having 1 or 2 ether groups (—O—). More specific examples thereof include dibutyl ether, dihexyl ether, dioctyl ether, ethylene glycol diethyl ether and the like.

Examples of the aforementioned esters include a mono-, di- or tri-ester with 6 or more and 36 or less carbons in total. More specific examples thereof include methyl laurate, isopropyl myristate, dihexyl malonate, triglyceride octanoate and the like.

Examples of the oil component include more preferably a compound represented by the following general formula (3):

$$R^4—(X)_{n'}—R^5 \quad (3)$$

Wherein $R^4$ and $R^5$ are hydrocarbon groups and the total of their numbers of carbons is 4 or more and 24 or less; X is a group selected from —O— and —COO—; n is a number selected from 0 and 1; and $R^4$, $R^5$ and n' are selected such that the compound has a solubility in water of 1 g/100 g or less at 25° C. and the compound turns liquid at 25° C.

The total of the numbers of carbons of $R^4$ and $R^5$ is 4 or more, preferably 6 or more and more preferably 10 or more from the viewpoint of enabling the clear judgement on the phase structure change, and 24 or less, preferably 20 or less and more preferably 18 or less from the same viewpoint. Examples of the hydrocarbon groups of $R^4$ and $R^5$ include an alkyl group, an alkenyl group and an aryl group. The numbers of carbons of $R^4$ and $R^5$ may be the same or different. n' is preferably 0.

In the present invention, the oil component is more preferably a hydrocarbon with 10 or more and 16 or less carbons.

At the time of preparing the calibration curve, first, the precursor sample is prepared by mixing water and surfactant (G) such that the concentration of surfactant (G) is the same as that of the surfactant in the aqueous sample. Next, the standard sample is prepared by adding the oil component to the precursor sample. Here, the added amount of the oil component can be determined on the basis of an amount of the precursor sample and the concentration of surfactant (G) in the precursor sample. The added amount of the oil component can be determined, for example, by the following formula (I):

Added amount of oil component (g)=mass of precursor sample (g)/100×concentration of surfactant (*G*) in precursor sample (mmol/kg)/*X*  formula (I)

In formula (I), X is a number of 0.1 or more, preferably 1 or more and more preferably 25 or more, and 1000 or less, preferably 500 or less and more preferably 250 or less.

The added amount of the oil component affects a change of a phase structure of the standard sample. Usually, there is such a tendency that the smaller a value of X in formula (I) is (i.e., the larger the added amount of the oil component is), the harder Om (a phase in which oil is a continuous phase) is to form, and on the other hand, the larger a value of X is (i.e., the smaller the added amount of the oil component is), the larger the number of phases constituting a phase structure is. It is preferable from the viewpoint of easily distinguishing the phase structure change that X be selected in simultaneous consideration of this tendency and an HLB value of surfactant (G). In the present invention, the phase structure change which is easiest to distinguish, especially by visual observation, is a change from a micellar solution phase (Wm phase) to a composite phase of a reversed micellar oil solution phase (Om phase) and a water phase (W phase), or a change from a micellar solution phase (Wm phase) to a composite phase of a bicontinuous phase (D phase) and a water phase (W phase). X preferable for causing such a phase structure change can be selected from numbers of 5 or more, further 10 or more and further 25 or more, and 500 or less, further 250 or less and further 100 or less.

To the standard sample prepared in such a manner, the phase-changing probe is added to quantify an amount of the phase-changing probe required until a phase structure of the standard sample changes.

As mentioned above, the phase structure of the standard sample before adding the phase-changing probe can include one or more structures selected from an oil phase (O phase), a reversed micellar oil solution phase (Om phase), a bicontinuous phase (D phase), a micellar solution phase (Wm phase) and a water phase (W phase).

When a certain kind of surfactant (G) is used, the phase structure of the standard sample before adding the phase-changing probe (hereinafter sometimes also referred to as the initial phase structure) turns into, as an example, a mixed system of an oil phase (O phase) and a micellar solution phase (Wm phase). When a certain kind of phase-changing probe is added to the standard sample having this phase structure, the phase structure changes from the aforementioned mixed system to a micellar solution phase (Wm phase), and according to the circumstances, next, a bicontinuous phase (D phase), and then, a mixed system of a reversed micellar oil solution phase (Om phase) and a water phase (W phase), and so on. In the present invention, it is preferable from the viewpoint of the accuracy of the calibration curve that the calibration curve be prepared by adopting added amounts of the phase-changing probe at the point of time when the phase structure of the standard sample changes from a micellar solution phase (Wm phase) to a mixed system of a reversed micellar oil solution phase (Om phase) and a water phase (W phase).

In the case where the initial phase structure of the standard sample is relatively rich in hydrophilicity, for example, in the case where it is a micellar solution phase (Wm phase) or a mixed system of an oil phase (O phase) and a micellar solution phase (Wm phase) with a proportion of the micellar solution phase (Wm phase) relatively high, such a compound as enhances the hydrophobicity of the standard sample, for example, 2-ethylhexyldiglycol is preferably used as the phase-changing probe.

On the other hand, in the case where the initial phase structure of the standard sample is relatively rich in hydrophobicity, for example, in the case where it is a mixed system of a reversed micellar oil solution phase (Om phase) and a water phase (W phase) with a proportion of the reversed micellar oil solution phase (Om phase) relatively high, such a compound as enhances the hydrophilicity of the standard sample, for example, butyldiglycol is preferably used as the phase-changing probe.

The standard sample can optionally contain a solvent. The solvent is used for the purpose of modifying a liquid property of the standard sample to be hydrophilic to suppress the gelation or the formation of crystals. In addition, such modification of a liquid property of the standard sample to be hydrophilic usually turns a phase structure of the standard sample into a structure relatively rich in hydrophilicity, so that it becomes easy to select the phase-changing probe.

The solvent is preferably an organic compound having a property that a solubility in water is high.

The solvent is preferably an organic solvent with a LogPow of preferably −1 or more, more preferably −0.5 or more and further preferably 0 or more from the viewpoint of suppressing the gelation or the formation of crystals, and preferably 1.5 or less and more preferably 1.0 or less from the same viewpoint. In the present invention, the logPow value is the coefficient indicating affinities of an organic compound for water and 1-octanol. The 1-octanol/water partition coefficient P is, in a distribution equilibrium caused when a trace amount of compound is dissolved as a solute in the solvents of the two liquid phases of 1-octanol and water, a ratio between equilibrium concentrations of the compound in the respective solvents, and generally represented in the form of logPow, which is the logarithm thereof to base 10. logPow values for many compounds have been reported and so many values are listed in databases available from Daylight Chemical Information Systems, Inc. (Daylight CIS) and the like that can be referred to. If there is no measured logPow value, it can be calculated by a program "CLOGP" available from Daylight CIS or the like. This program outputs a value of "calculated logPow (ClogPow)" calculated by Hansch and Leo's fragment approach together with a measured logPow value if any.

Specifically, the solvent is favorably a monoalcohol with 2 or more and 8 or less carbons, a glycol with 2 or more and 8 or less carbons, a mono-, di-, tri- or tetra-glycol ether having one alkyl group with 2 or more and 8 or less carbons. From the viewpoint of suppressing the gelation or the formation of crystals, it is more preferably a solvent selected from ethanol, propanol, ethylene glycol, propylene glycol, butylene glycol and mono-, di- or tri-glycol ethers having one alkyl group with 1 or more and 5 or less carbons.

From the viewpoint of suppressing the gelation or the formation of crystals, an added amount of the solvent is preferably 1 mass % or more and more preferably 1.5 mass % or more, and preferably 20 mass % or less, more preferably 15 mass % or less, further preferably 10 mass % or less and furthermore preferably 8 mass % or less relative to the precursor sample.

While the addition of the phase-changing probe to a standard sample may be performed at a predetermined temperature, for example, at an environmental temperature of 25° C., this temperature condition is also applied to the case where an amount of the phase-changing probe is quantified for another standard sample. Note that environmental temperatures at the time of adding the phase changing probe to an aqueous sample and at the time of quantifying an amount of the phase-changing probe for a standard sample may be the same or different.

The addition of the phase-changing probe to the standard sample is preferably performed under stirring. For the stirring, for example, a magnetic stirrer, a mechanical stirrer, a vibration stirrer or the like can be used. The stirring device or working conditions thereof is also applied to the case where an amount of the phase-changing probe is quantified for another standard sample or an aqueous sample.

A phase structure change of the standard sample can be visually checked. For example, when an appearance of the standard sample turns from one colorless or slightly-bluish transparent phase (Wm phase) before a phase-changing probe is added to two whitish phases (a mixed system of Om phase and W phase or a mixed system of D phase and W phase), it can be judged that the phase structure has changed. In addition, a phase structure change of the standard sample can also be checked by, for example, observing an inflection point in a change of transmittance of an ultraviolet visible spectrophotometer. Further, a phase structure change of the standard sample can also be checked by, for example, observing an inflection point in a change of turbidity using a turbidimeter. For example, when a transparent or translucent sample drastically turns turbid and the transmittance or turbidity drastically changes at a stage where a certain amount of the phase-changing probe has been added during its gradual addition, it can be judged that a non-continuous change has occurred to change the phase structure. Further, the amount of the phase-changing probe is recorded when the phase structure changes.

According to the same procedure, quantitative values of the phase changing probe when a phase structure of the standard sample changes are obtained respectively for a plurality of surfactants with different Griffin's HLB values. Any of the respective quantitative values is obtained by performing the measurement under the same conditions.

A calibration curve is prepared from the plurality of quantitative values obtained and the HLB values of the surfactants included in the standard samples that provide the quantitative values. The calibration curve is usually obtained as a regression line by the least squares method.

Next, an amount of the phase-changing probe is also quantified for the aqueous sample whose physical property is to be estimated. Specifically, the same oil component and optional solvent as those added to the precursor sample at the time of preparing the calibration curve are added to the aqueous sample in the same respective amounts as those in the precursor sample to prepare a measurement sample. The same phase-changing probe as the one used for the measurement of the quantitative values of the calibration curve is added to the measurement sample, and an amount of the phase-changing probe required until a phase structure of the measurement sample changes is quantified. The operating conditions are the same as those for the preparation of the calibration curve.

By applying a quantitative value of the phase-changing probe obtained for the measurement sample to the calibration curve, the corresponding HLB-axis value is determined. The value determined as the HLB value of this surfactant is not the exact HLB value of the surfactant in the aqueous sample used for the measurement sample. However, it can be understood as an indicator for indicating a liquid physical property of the aqueous sample because a phase structure caused by a certain amount of the phase-changing probe is the same between the standard sample and the measurement sample, so that the measurement sample can be regarded as indicating the same solution physical property as that of the standard sample in which surfactant (G) is dissolved. In the present invention, with the HLB-axis values in the calibration curve defined as liquid physical property indexes, a physical property of the aqueous sample is estimated from a liquid physical property index corresponding to a quantitative value of the phase-changing probe for the measurement sample.

In the present invention, a physical property can be estimated in a simple manner, not only when the aqueous sample is a simple surfactant solution, but also when it is a complicated system containing a salt, a polymer compound, an acid and the like. In addition, a change in the hydrophilicity or hydrophobicity of the system due to a change in temperature can also be estimated preferably on the basis of the solution physical property index of the present invention.

The concentration of the surfactant in the aqueous sample may be, for example, 1 mmol/kg or more, further 5 mmol/kg or more and further 50 mmol/kg or more, and 500 mmol/kg or less, further 350 mmol/kg or less and further 200 mmol/kg or less.

Note that examples of the surfactant contained in the aqueous sample include one or more surfactants selected from nonionic surfactants, anionic surfactants, cationic surfactants and amphoteric surfactants. As the respective surfactants, publicly-known surfactants can be appropriately used. As a nonionic surfactant, the one corresponding to surfactant (G) can be used. The type, combination, concentration and the like of the surfactants can be appropriately selected in view of the application of the aqueous sample and the like.

[Method for Producing Liquid Composition]

The method for estimating a physical property of an aqueous sample of the present invention can be incorporated into a method for producing a liquid composition having a desired physical property.

The present invention provides a method for producing a liquid composition with a desired physical property containing a surfactant and water, including:
estimating, by the method of the present invention, a physical property of an aqueous composition containing a surfactant and water, the surfactant being at least one surfactant with which the final liquid composition is formulated; and
in response to the estimated physical property, determining whether or not to change the composition of the aqueous composition.

The matters mentioned in the method for estimating a physical property of an aqueous sample of the present invention can be appropriately applied to the method for producing a liquid composition of the present invention.

In the producing method of the present invention, an aqueous composition containing a surfactant and water, the surfactant being at least one surfactant with which the final liquid composition is formulated, is subjected to the estimation of a physical property by the method of the present invention as an aqueous sample. For example, in the case where the final liquid composition needs to have a certain desired hydrophobicity, a hydrophobicity of the aforementioned aqueous composition is estimated by the method of the present invention, and in response to the result, formulation components are adjusted in such a manner that the hydrophobicity of the aqueous composition is increased or decreased. How the formulation components contribute to the hydrophobicity of the aqueous composition can be determined, for example, on the basis of findings known in fields using liquid compositions.

In the producing method of the present invention, the liquid composition may be a detergent composition. That is, the producing method of the present invention can be implemented as a method for producing a detergent composition. Examples of the detergent composition include a detergent composition for hard surfaces, a detergent composition for clothes, a body detergent composition and the like.

Further, in the producing method of the present invention, the liquid composition may be a cosmetic composition. That is, the producing method of the present invention can be implemented as a method for producing a cosmetic composition. Examples of the cosmetic composition include a hair cosmetic composition, a skin cosmetic composition, a finishing cosmetic composition, perfume, eau de cologne and the like.

The producing method of the present invention can be applied to methods for producing various compositions containing a surfactant and water such as a treatment agent composition for textile products, an aromatic composition, a bactericide composition, an agricultural composition and the like.

[Method for Adjusting Physical Property of Aqueous Composition]

The method for estimating a physical property of an aqueous sample of the present invention can be incorporated into a method for adjusting a physical property of an aqueous composition.

The present invention provides a method for adjusting a physical property of an aqueous composition, including:
estimating a physical property of an aqueous composition containing a surfactant and water by the method of the present invention; and
in response to the estimated physical property, changing the composition of the aqueous composition to adjust the physical property of the aqueous composition.

The matters mentioned in the method for estimating a physical property of an aqueous sample of the present invention can be appropriately applied to the method for adjusting a physical property of an aqueous composition of the present invention.

Like the producing method of the present invention, also in the adjusting method of the present invention, a physical property of an aqueous composition is estimated by the method of the present invention, and in response to the result, the composition of the aqueous composition is changed in such a manner that the physical property of the aqueous composition reaches a desired degree. How to change the composition can be determined in view of formulation components and the like, for example, on the basis of findings known in fields using aqueous compositions.

[Method for Preparing Calibration Curve]

The present invention provides a method for preparing a calibration curve for estimating a physical property of an aqueous sample containing a predetermined concentration of surfactant and water from an amount of a phase-changing probe added to the aqueous sample, including:
preparing a standard sample by adding an oil component and optionally a solvent to a precursor sample containing water and a surfactant with a known Griffin's HLB value, the concentration of the surfactant with a known Griffin's HLB value being the same as the concentration of the surfactant in the aqueous sample;
adding to the standard sample the phase-changing probe composed of a compound having a different structure than that of the surfactant with a known Griffin's HLB value to quantify an amount of the phase-changing probe required until a phase structure of the standard sample changes, and performing this quantification for a plurality of surfactants with different Griffin's HLB values under the same conditions to obtain a plurality of quantitative values; and preparing the calibration curve from the quantitative values and the HLB values of the surfactants included in the standard samples that provide the quantitative values.

This preparation method can be implemented in the same manner as the preparation of a calibration curve in the method for estimating a physical property of an aqueous sample of the present invention. Specific operations, specific examples or preferable modes of the respective components, or the like are the same as those in the method for estimating a physical property of an aqueous sample of the present invention.

The matters mentioned in the method for estimating a physical property of an aqueous sample of the present invention can be appropriately applied to the method for preparing a calibration curve of the present invention.

[Apparatus for Estimating Physical Property of Aqueous Sample]

The present invention provides an apparatus for estimating a physical property of an aqueous sample containing a predetermined concentration of surfactant and water from an amount of a phase-changing probe added to the aqueous sample, including:

a measurement unit to measure an added amount of the phase-changing probe; an input unit to input the added amount of the phase-changing probe; a calibration curve acquisition unit to acquire a calibration curve from input measurement values; and a determination unit to determine a physical property of the aqueous sample by applying an added amount of the phase-changing probe to the calibration curve, wherein the measurement unit includes: a container to contain the aqueous sample or a standard sample containing a surfactant with a known Griffin's HLB value, an oil component, water and optionally a solvent; a supply device to add to the aqueous sample or the standard sample the phase-changing probe composed of a compound having a different structure than that of the surfactant with a known Griffin's HLB value; and a recording device to record an added amount of the phase-changing probe required until a phase structure of the aqueous sample or the standard sample changes, the measurement unit acquires a plurality of amounts (I) of the phase-changing probe added for a plurality of surfactants with different Griffin's HLB values under the same conditions, and the added amounts (I) are input to the calibration curve acquisition unit as the measurement values to acquire the calibration curve, and the determination unit includes a determination device to acquire, on the basis of an added amount (II), received from the recording device, of the phase-changing probe required until a phase structure of the aqueous sample changes, a Griffin's HLB value corresponding to the added amount (II) in the calibration curve.

The matters mentioned in the method for estimating a physical property of an aqueous sample of the present invention can be appropriately applied to the apparatus of the present invention.

The apparatus of the present invention can be used in the method for estimating a physical property of an aqueous sample of the present invention.

The measurement unit to measure an added amount of the phase-changing probe includes: a container to contain an aqueous sample or a standard sample; a supply device to add the phase-changing probe to the aqueous sample or the standard sample; and a recording device to record an added amount of the phase-changing probe required until a phase structure of the aqueous sample or the standard sample changes.

The shape or size of the container is not specified.

As the supply device, for example, a device including a publicly-known structure capable of transporting a liquid component can be used.

As the quantifying device, for example, a device including a publicly-known structure capable of monitoring and quantifying a supply amount of a liquid component can be used.

The measurement unit acquires a plurality of amounts of the phase-changing probe added for a plurality of surfactants with different Griffin's HLB values under the same conditions.

As the input unit to input an added amount of the phase-changing probe, for example, a device including a publicly-known structure capable of recording information received from the quantifying device.

As the calibration curve acquisition unit to acquire a calibration curve from input measurement values, for example, a publicly-known device including processing software and a computer to process and plot the measurement values can be used.

The determination unit determines a physical property of an aqueous sample by applying to the calibration curve an added amount of the phase-changing probe required until a phase structure of the aqueous sample changes. The determination unit includes a determination device to acquire a Griffin's HLB value corresponding to added amount (II) in the calibration curve. As the determination device, for example, a publicly-known device including processing software and a computer to perform the process of applying added amount (II) to the calibration curve to acquire the corresponding Griffin's HLB value can be used.

In addition, it is also possible to incorporate a device for preparing a calibration curve into an apparatus for estimating a physical property of an aqueous sample. As the apparatus for estimating a physical property of an aqueous sample, the one configured from: a measurement unit to measure an added amount of a phase-changing probe; an input unit to input the added amount of the phase-changing probe; and a unit to acquire a physical property of an aqueous sample from the added amount of the phase-changing probe and a calibration curve prepared by the device for preparing a calibration curve can be used. The measurement unit and the input unit may be integrated into the same device with the device for preparing a calibration curve or different devices may be used for them. As the unit to acquire a physical property of an aqueous sample, a publicly-known device including processing software and a computer can be used.

In another aspect, the present invention provides an apparatus for preparing a calibration curve for estimating a physical property of an aqueous sample containing a predetermined concentration of surfactant and water from an amount of a phase-changing probe added to the aqueous sample, including:

a measurement unit to measure an added amount of the phase-changing probe; an input unit to input the added amount of the phase-changing probe; and a calibration curve acquisition unit to acquire a calibration curve from input measurement values;

wherein the measurement unit includes: a container to contain a standard sample containing a surfactant with a known Griffin's HLB value, an oil component, water and optionally a solvent; a supply device to add to the standard sample the phase-changing probe composed of a compound having a different structure than that of the surfactant with a known Griffin's HLB value; and a recording device to record an added amount of the phase-changing probe required until a phase structure of the standard sample changes, the measurement unit acquires a plurality of amounts of the phase-changing probe added for a plurality of surfactants with different Griffin's HLB values under the same conditions, and added amounts (I) are input to the calibration curve acquisition unit as the measurement values to acquire the calibration curve.

[Kit for Preparing Calibration Curve]

The present invention provides a calibration curve preparation kit for preparing a calibration curve for estimating a physical property of an aqueous sample containing a predetermined concentration of surfactant and water from an amount of a phase-changing probe added to the aqueous sample, including:

a plurality of standard samples each containing a surfactant with a known Griffin's HLB value, an oil component, water and optionally a solvent; and a phase-changing probe composed of a compound having a different structure than that of the surfactant with a known Griffin's HLB value, wherein the plurality of standard samples are of the same composition except that the Griffin's HLB values of the surfactants are different from one another, and in each of the plurality of standard samples, the concentration of the surfactant with a known Griffin's HLB value in the total of the surfactant with a known Griffin's HLB value and water is the same as the concentration of the surfactant in the aqueous sample.

Specific examples and preferable modes of the components in the standard sample and the phase-changing probe in the calibration curve preparation kit of the present invention are the same as those in the method for estimating a physical property of an aqueous sample of the present invention.

The matters mentioned in the method for estimating a physical property of an aqueous sample of the present invention can be appropriately applied to the calibration curve preparation kit of the present invention.

The calibration curve preparation kit of the present invention can be used for the preparation of a calibration curve used in the present invention.

EXAMPLES

Example 1

Using the following components, precursor samples and standard samples for preparing calibration curves were prepared, and using any of the following phase-changing probes, an amount of the phase-changing probe required until a phase structure of a standard sample changed was quantified for each of a plurality of surfactants (G). The calibration curves were prepared from the plurality of quantitative values obtained.

Surfactant (G): a plurality of polyoxyethylene lauryl ethers with different average numbers of added moles of the ethylene oxide Oil component: an isoparaffin with an average number of carbons of 16 (hereinafter, referred to as C16 isoparaffin)

Phase-changing probe: 2-ethylhexyl diglycol or butyldiglycol

The concentration of surfactant (G) in each precursor sample was 200 mmol/kg (the balance was water).

The amount of the oil component added per 100 g of each precursor sample was determined to be 4 g by assigning 50 to X in the aforementioned formula (I).

In the case where an average number of added moles of the ethylene oxide of surfactant (G) was relatively large (the average number of added moles was 6 to 21), the initial phase structure of the standard sample was a mixed system of an oil phase (O phase) and a micellar solution phase (Wm phase). For this standard sample, 2-ethylhexyl diglycol (hereinafter, sometimes also referred to as 2-EHDG) was used as the phase-changing probe, and an amount of the phase-changing probe required until a phase structure of the standard sample changed from a micellar solution phase (Wm phase) to a mixed system of a reversed micellar oil solution phase (Om phase) and a water phase (W phase) was taken as the quantitative value.

On the other hand, in the case where an average number of added moles of the ethylene oxide of surfactant (G) was relatively small (the average number of added moles was 2 to 5), the initial phase structure of the standard sample was a mixed system of a reversed micellar oil solution phase (Om phase) and a water phase (W phase). For this standard sample, butyldiglycol (hereinafter, sometimes also referred to as BDG) was used as the phase-changing probe, and an amount of the phase-changing probe required until a phase structure of the standard sample changed from a mixed system of a reversed micellar oil solution phase (Om phase) and a water phase (W phase) to a micellar solution phase (Wm phase) was taken as the quantitative value.

Note that, in either case, the ambient temperature when the phase-changing probe was added to the standard sample was 25° C. Further, in either case, the phase-changing probe was added to the standard sample under the condition of being stirred with a magnetic stirrer.

Quantitative values in the case where 2-EHDG was used as the phase-changing probe and those in the case where BDG was used as the phase-changing probe are shown in Tables 1 and 2, respectively.

Note that the quantitative values and HLB values were entered into spreadsheet software "Excel" (manufactured by Microsoft Corporation) to be processed, thereby obtaining the calibration curves as regression lines (calibration curves 1 and 2). Calibration curves 1 and 2 are shown in Graph A (FIG. 1).

As a result, it was found that the highly-linear calibration curves were obtained even if the initial phase structures were different or the phase changes caused by adding the phase-changing probes were different.

TABLE 1

| Polyoxyethylene lauryl ether | | Quantitative value (g) |
| --- | --- | --- |
| Average number of added moles of EO | HLB | of phase-changing probe (2-EHDG) |
| 6 | 11.73 | 1.7 |
| 9 | 13.61 | 5.38 |
| 12 | 14.79 | 7.4 |
| 21 | 16.65 | 11.92 |
| Calibration curve prepared | | Calibration curve 1 |

TABLE 2

| Polyoxyethylene lauryl ether | | Quantitative value (g) of phase-changing probe (BDG) |
|---|---|---|
| Average number of added moles of EO | HLB | |
| 2 | 6.42 | 18.57 |
| 3 | 8.30 | 13.2 |
| 4 | 9.72 | 7.29 |
| 5 | 10.83 | 5.5 |
| Calibration curve prepared | | Calibration curve 2 |

Example 2

(1) Preparation of Calibration Curve

Calibration curves 3 to 7 were prepared in the same manner as in Example 1 except that oil components were variously changed.

As the oil components, components shown in Table 3 were used; as the phase-changing probe, 2-EHDG was used; and the concentration of surfactant (G) in each precursor sample was 100 mmol/kg. Note that, in this example, the amount of an oil component added per 100 g of each precursor sample was determined to be 2 g by assigning 50 to X in the aforementioned formula (I).

In this example, the initial phase structure of a standard sample was a mixed system of an oil phase (O phase) and a micellar solution phase (Wm phase), and an amount of the phase-changing probe required until a phase structure of the standard sample changed from a micellar solution phase (Wm phase) to a mixed system of a reversed micellar oil solution phase (Om phase) and a water phase (W phase) was taken as a quantitative value.

Quantitative values of the phase-changing probe are shown in Table 3. In addition, calibration curves 3 to 7 are shown in Graphs B to F (FIGS. 2 to 6).

As a result, it was found that highly-linear calibration curves were obtained even if the oil components were different.

(2) Estimation of Physical Property of Aqueous Sample

An aqueous sample containing N-lauryl-N, N-dimethyl-N-(2-hydroxysulfopropyl) ammonium sulfobetaine at a concentration of 100 mmol/kg (the balance was water) was prepared.

A measurement sample was prepared by adding 2 g of any of the oil components shown in Table 3 per 100 g of the aqueous sample.

2-EHDG as the phase-changing probe was added to the measurement sample under the same conditions as those for preparing the calibration curves, and an amount of the phase-changing probe required until a phase structure changed was quantified.

In this example, the initial phase structure of the measurement sample was a mixed system of an oil phase (O phase) and a micellar solution phase (Wm phase), and an amount of the phase-changing probe required until a phase structure of the measurement sample changed from a micellar solution phase (Wm phase) to a mixed system of a reversed micellar oil solution phase (Om phase) and a water phase (W phase) was taken as a quantitative value. The quantitative value was applied to the calibration curve for which the same oil component was used, thereby obtaining the corresponding liquid physical property index (corresponding HLB value). The results are shown in Table 4.

As a result, it was found that, for the aqueous sample containing N-lauryl-N, N-dimethyl-N-(2-hydroxysulfopropyl) ammonium sulfobetaine at a concentration of 100 mmol/kg, even if the different oil components were used, resultant solution physical property indexes (corresponding HLB values) were 11.30-11.52, that is, almost the same values.

TABLE 3

| Polyoxyethylene lauryl ether | | Quantitative value (g) of phase-changing probe (2-EHDG) | | | | |
|---|---|---|---|---|---|---|
| Avarage number | | Oil component | | | | |
| of added moles of EO | HLB | C16 isoparaffin | Decane | Tetradecane | Hexadecane | Cyclohexane |
| 6 | 11.73 | 2.96 | 2.78 | 3.2 | 3.4 | 1.96 |
| 9 | 13.61 | 7.58 | 6.98 | 7.6 | 7.74 | 5.84 |
| 12 | 14.79 | 10.24 | 9.4 | 10.02 | 10.24 | 8.24 |
| Calibration curve prepared | | Calibration curve 3 | Calibration curve 4 | Calibration curve 5 | Calibration curve 6 | Calibration curve 7 |

TABLE 4

| | Oil component | | | | |
|---|---|---|---|---|---|
| | C16 isoparaffin | Decane | Tetradecane | Hexadecane | Cyclohexane |
| Quantitative value (g) of phase-changing probe (2-EHDG) | 2.36 | 2.36 | 2.66 | 2.78 | 1.15 |
| Calibration curve | Calibration curve 3 | Calibration curve 4 | Calibration curve 5 | Calibration curve 6 | Calibration curve 7 |
| Solution physical property index (corresponding HLB) from calibration curve | 11.46 | 11.52 | 11.47 | 11.44 | 11.30 |

Example 3

Calibration curves 8 and 9 were prepared in the same manner as in Example 1 except that concentrations of surfactant (G) in precursor samples were variously changed.

The phase-changing probe was 2-EHDG and the concentration of surfactant (G) in a precursor sample was 5 mmol/kg or 350 mmol/kg. When the concentration of surfactant (G) in a precursor sample was 5 mmol/kg, an amount of the oil component added per 100 g of the precursor sample was 0.1 g (X in formula (I)=50). When the concentration of surfactant (G) in a precursor sample was 350 mmol/kg, an amount of the oil component added per 100 g of the precursor sample was 7 g (X in formula (I)=50).

In this example, the initial phase structure of a standard sample was a mixed system of an oil phase (O phase) and a micellar solution phase (Wm phase), and an amount of the phase-changing probe required until a phase structure of the standard sample changed from a micellar solution phase (Wm phase) to a mixed system of a reversed micellar oil solution phase (Om phase) and a water phase (W phase) was taken as a quantitative value.

Figure 7:
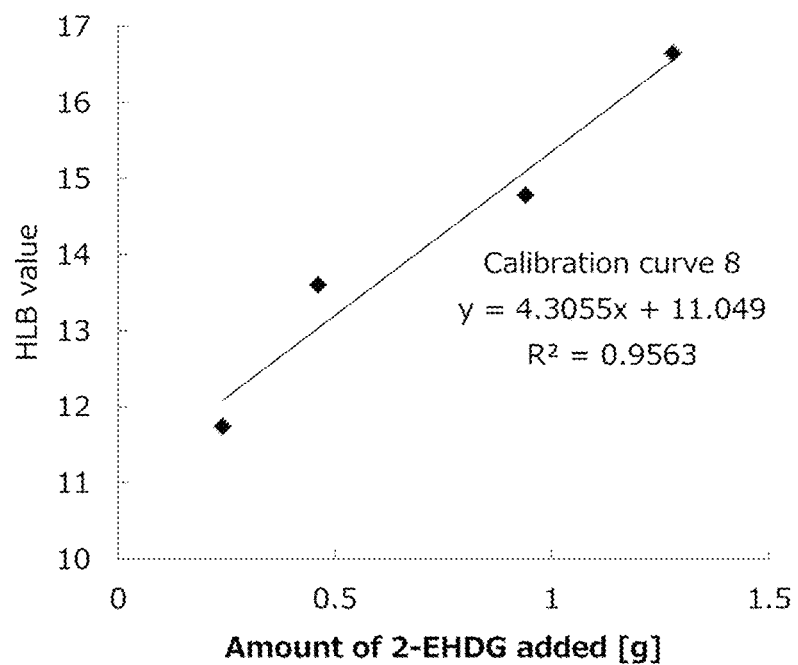
FIG. 7 shows Graph G containing calibration curve 8.
Figure 8:
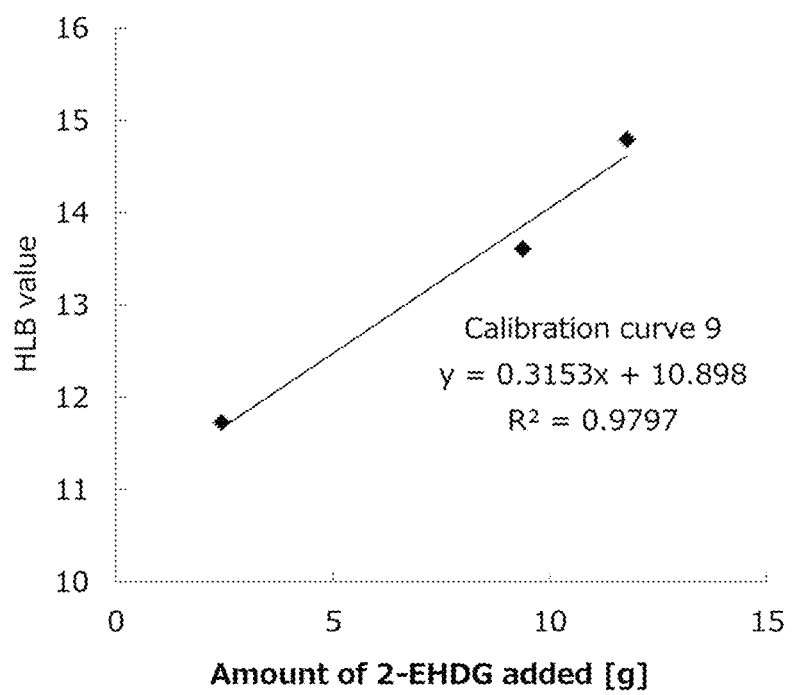
FIG. 8 shows Graph H containing calibration curve 9.

Quantitative values of the phase-changing probe are shown in Table 5. In addition, calibration curves 8 and 9 are shown in Graphs G and H (FIGS. 7 and 8).

As a result, it was found that highly-linear calibration curves were obtained even if the concentrations of the surfactant in the precursor samples were varied.

TABLE 5

| Polyoxyethylene lauryl ether | | Quantitative value (g) of phase-changing probe (2-EHDG) Concentration of polyoxyethylene lauryl ether | |
|---|---|---|---|
| Average number of added moles of EO | HLB | 5 mmol/kg | 350 mmol/kg |
| 6 | 11.73 | 0.24 | 2.44 |
| 9 | 13.61 | 0.46 | 9.36 |
| 12 | 14.79 | 0.94 | 11.76 |
| 21 | 16.65 | 1.28 | ☐ |
| Calibration curve prepared | | Calibration curve 8 | Calibration curve 9 |

Example 4

Using the following components, precursor samples and standard samples for preparing a calibration curve were prepared, and using the following phase-changing probe, an amount of the phase-changing probe required until a phase structure of a standard sample changed was quantified for each of a plurality of surfactants (G). The calibration curve was prepared from the plurality of quantitative values obtained.

Surfactant (G): a plurality of polyoxyethylene lauryl ethers with different average numbers of added moles of the ethylene oxide
Solvent: BDG
Oil component: C16 isoparaffin
Phase-changing probe: 2-EHDG The concentration of surfactant (G) in each precursor sample was 100 mmol/kg (the balance was water).

The added amount of the solvent was 5 mass % relative to each precursor sample (the total of surfactant (G) and water).

The amount of the oil component added per 100 g of each precursor sample was determined to be 2 g by assigning 50 to X in the aforementioned formula (I).

Figure 9:
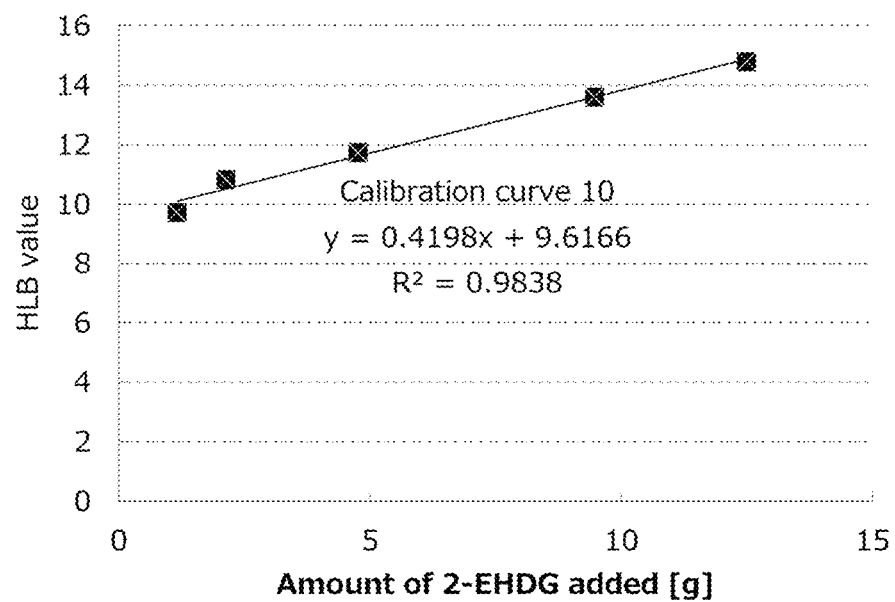
FIG. 9 shows Graph I containing calibration curve 10.

The initial phase structure of a standard sample was a mixed system of an oil phase (O phase) and a micellar solution phase (Wm phase). In this example, an amount of the phase-changing probe required until a phase structure of the standard sample changed from a micellar solution phase (Wm phase) to a mixed system of a reversed micellar oil solution phase (Om phase) and a water phase (W phase) was taken as a quantitative value. Quantitative values are shown in Table 6. Note that the ambient temperature when the phase-changing probe was added to the standard sample was 25° C. Further, the phase-changing probe was added to the standard sample under the condition of being stirred with a magnetic stirrer. The quantitative values and HLB values were entered into spreadsheet software "Excel" (manufactured by Microsoft Corporation) to be processed, thereby obtaining the calibration curve as a regression line (calibration curve 10). Calibration curve 10 is shown in Graph I (FIG. 9).

TABLE 6

| Polyoxyethylene lauryl ether | | Quantitative value (g) |
|---|---|---|
| Average number of added moles of EO | HLB | of phase-changing probe (2-EHDG) |
| 4 | 9.72 | 1.16 |
| 5 | 10.83 | 2.12 |
| 6 | 11.73 | 4.76 |
| 9 | 13.61 | 9.46 |
| 12 | 14.79 | 12.5 |
| Calibration curve prepared | | Calibration curve 10 |

Example 5

A physical property of an aqueous sample containing a surfactant shown in Table 7 was estimated by using calibration curve 10.

In any aqueous sample, the concentration of a surfactant shown in Table 7 was 100 mmol/kg (the balance was water).

BDG as the solvent was added in an amount of 5 mass % to the aqueous sample (relative to a mass of the aqueous sample).

A measurement sample was prepared by adding 2 g of C16 isoparaffin as the oil component per 100 g of the aqueous sample.

2-EHDG as the phase-changing probe was added to the measurement sample under the same conditions as those for preparing calibration curve 10, and an amount of the phase-changing probe required until a phase structure changed was quantified.

In this example, the initial phase structure of the measurement sample was a mixed system of an oil phase (O phase) and a micellar solution phase (Wm phase), and an amount of the phase-changing probe required until a phase structure of the measurement sample changed from a micellar solution phase (Wm phase) to a mixed system of a reversed micellar oil solution phase (Om phase) and a water phase (W phase) was determined as a quantitative value. The quantitative value was applied to calibration curve 10, thereby obtaining the corresponding liquid physical property index (corresponding HLB value). The results are shown in Table 7.

As a result, it was found that a physical property of an aqueous sample containing an anionic surfactant, an amine oxide-type surfactant or a cationic surfactant can be estimated on the basis of the liquid physical property index (corresponding HLB value).

TABLE 7

| Surfactant in aqueous sample | Quantitative value (g) of phase-changing probe (2-EHDG) | Solution physical property index (corresponding HLB) from calibration curve 10 |
|---|---|---|
| N-lauryl-N,N-dimethyl-N-(2-hydroxysulfopropyl)ammonium sulfobetaine | 3.60 | 11.13 |
| Sodium di-2-ethylhexylsulfosuccinate | 5.50 | 11.93 |
| Lauryl glucoside (average degree of condensation of sugars: 1.3) | 4.44 | 11.48 |
| Lauryl dimethylamine oxide | 5.04 | 11.73 |
| Myristyl dimethylamine oxide | 4.72 | 11.60 |
| Sodium linear alkyl (main constituent: C12) benzene sulfonate (molecular weight: 345) | 19.56 | 17.83 |
| Sodium dodecyl sulfate | 21.76 | 18.75 |
| Sodium polyoxyethylene (2 moles on average) lauryl ether sulfate | 17.68 | 17.04 |
| Sodium polyoxyethylene (4 moles on average) lauryl ether sulfate | 19.88 | 17.96 |
| Octyldimethylbenzylammonium chloride | 9.20 | 13.48 |
| Lauryldimethylbenzylammonium chloride | 10.36 | 13.97 |
| Lauryltrimethylammonium chloride | 11.04 | 14.25 |
| Palmityltrimethylammonium chloride | 9.12 | 13.45 |

Example 6

A physical property of an aqueous sample of composition shown in Table 8 was estimated by using calibration curve 1.

In any aqueous sample, the total concentration of surfactants shown in Table 8 was 200 mmol/kg.

A measurement sample was prepared by adding 2 g of C16 isoparaffin as the oil component per 100 g of the aqueous sample.

2-EHDG as the phase-changing probe was added to the measurement sample under the same conditions as those for preparing calibration curve 1, and an amount of the phase-changing probe required until a phase structure changed was quantified.

In this example, the initial phase structure of the measurement sample was a mixed system of an oil phase (O phase) and a micellar solution phase (Wm phase), and an amount of the phase-changing probe required until a phase structure of the measurement sample changed from a micellar solution phase (Wm phase) to a mixed system of a reversed micellar oil solution phase (Om phase) and a water phase (W phase) was taken as a quantitative value. The quantitative value was applied to calibration curve 1, thereby obtaining the corresponding liquid physical property index (corresponding HLB value). The results are shown in Table 8.

As a result, it was found that a physical property of the composition containing a plurality of surfactants and chelating agents can be estimated on the basis of the liquid physical property index (corresponding HLB value).

TABLE 8

| | | | Aqueous sample | | | | | | | | |
|---|---|---|---|---|---|---|---|---|---|---|---|
| | | | 1 | 2 | 3 | 4 | 5 | 6 | 7 | 8 | 9 |
| Composition of aqueous sample (mass %) | Surfactant | N-lauryl-N,N-dimethyl-N-(2-hydroxysulfopropyl) ammonium sulfobetaine | 3.16 | 3.16 | 3.16 | 3.16 | 3.16 | 3.16 | 3.16 | 3.16 | 3.16 |
| | | Sodium di-2-ethylhexylsulfosuccinate | 4.45 | 4.45 | 4.45 | 2.22 | 2.22 | 2.22 | 0.56 | 0.56 | 0.56 |
| | | 2-ethyl hexyl monoglyceryl ether | 0 | 0 | 0 | 1.02 | 1.02 | 1.02 | 1.79 | 1.79 | 1.79 |
| | | BDG | 7 | 9 | 12 | 7 | 8 | 12 | 5 | 7 | 11 |
| | | Citric acid | 1 | 1 | 1 | 1 | 1 | 1 | 1 | 1 | 1 |
| | | Propylene glycol | 5 | 5 | 5 | 5 | 5 | 5 | 5 | 5 | 5 |
| | | Water | Balance | Balance | Balance | Balance | Balance | Balance | Balance | Balance | Balance |
| | | Total | 100 | 100 | 100 | 100 | 100 | 100 | 100 | 100 | 100 |
| | Quantitative value (g) of phase-changing probe (2-EHDG) | | 0.33 | 2.44 | 4.08 | 0.7 | 2.06 | 4.14 | 0.96 | 2.46 | 4.2 |
| | Solution physical property index (corresponding HLB) from calibration curve 1 | | 11.2 | 12.2 | 13.0 | 11.3 | 12.0 | 13.0 | 11.5 | 12.2 | 13.0 |

Example 7

A physical property of an aqueous sample containing surfactants shown in Table 9 at proportions shown in Table 9 was estimated by using calibration curve 10.

In any aqueous sample, the total concentration of surfactants shown in Table 9 was 100 mmol/kg (the balance was water).

BDG as the solvent was added in an amount of 5 mass % to the aqueous sample (relative to a mass of the aqueous sample).

A measurement sample was prepared by adding 2 g of C16 isoparaffin as the oil component per 100 g of the aqueous sample.

2-EHDG as the phase-changing probe was added to the measurement sample under the same conditions as those for preparing calibration curve 10, and an amount of the phase-changing probe required until a phase structure changed was quantified.

In this example, the initial phase structure of the measurement sample was a mixed system of an oil phase (O phase) and a micellar solution phase (Wm phase), and an amount of the phase-changing probe required until a phase structure of the measurement sample changed from a micellar solution phase (Wm phase) to a mixed system of a reversed micellar oil solution phase (Om phase) and a water phase (W phase) was taken as a quantitative value. The quantitative value was applied to calibration curve 10, thereby obtaining the corresponding liquid physical property index (corresponding HLB value). The results are shown in Table 9.

As a result, it was found that a physical property of the composition prepared by mixing two types of surfactants at a different ratio can be estimated on the basis of the liquid physical property index (corresponding HLB value).

The aqueous sample which contained a surfactant and an inorganic salt shown in Table 10 at the respective concentrations shown in Table 10 was prepared.

BDG as the solvent was added in an amount of 5 mass % to the aqueous sample (relative to a mass of the aqueous sample).

A measurement sample was prepared by adding 2 g of C16 isoparaffin as the oil component per 100 g of the aqueous sample.

2-EHDG as the phase-changing probe was added to the measurement sample under the same conditions as those for preparing calibration curve 10, and an amount of the phase-changing probe required until a phase structure changed was quantified.

In this example, the initial phase structure of the measurement sample was a mixed system of an oil phase (O phase) and a micellar solution phase (Wm phase), and an amount of the phase-changing probe required until a phase structure of the measurement sample changed from a micellar solution phase (Wm phase) to a mixed system of a reversed micellar oil solution phase (Om phase) and a water phase (W phase) was taken as a quantitative value. The quantitative value was applied to calibration curve 10, thereby obtaining the corresponding liquid physical property index (corresponding HLB value). The results are shown in Table 10.

TABLE 9

| Surfactant in aqueous sample | | Quantitative value (g) of phase-changing probe | Solution physical property index (corresponding HLB) |
|---|---|---|---|
| Composition | Mass ratio | (2-EHDG) | from calibration curve 10 |
| Sodium dodecyl sulfate/lauryl dimethylamine oxide | 100/0 | 21.76 | 18.75 |
| | 75/25 | 6.40 | 12.30 |
| | 50/50 | 4.00 | 11.30 |
| | 25/75 | 2.58 | 10.70 |
| | 0/100 | 5.04 | 11.73 |
| Sodium dodecyl sulfate/ polyoxyethylene (6 moles on average) lauryl ether | 100/0 | 21.76 | 18.75 |
| | 75/25 | 19.24 | 17.69 |
| | 50/50 | 15.24 | 16.01 |
| | 25/75 | 11.27 | 14.35 |
| | 0/100 | 4.76 | 11.61 |
| Sodium dodecyl sulfate/ lauryltrimethylammonium chloride | 100/0 | 21.76 | 18.75 |
| | 75/25 | 4.70 | 11.59 |
| | 50/50 | 1.20 | 10.12 |
| | 25/75 | 4.54 | 11.52 |
| | 0/100 | 11.04 | 14.25 |

Example 8

A physical property of an aqueous sample containing a surfactant and an inorganic salt at proportions shown in Table 10 was estimated by using calibration curve 10.

As a result, it was found that a physical property of the composition prepared by adding a different amount of an inorganic salt to the composition containing the surfactant and water can be estimated on the basis of the liquid physical property index (corresponding HLB value).

TABLE 10

| Surfactant in aqueous sample | | Inorganic salt in aqueous sample | | Quantitative value (g) of phase-changing probe | Solution physical property index (corresponding HLB) |
|---|---|---|---|---|---|
| Type | Concentration (mmol/kg) | Type | Concentration (mmol/kg) | (2-EHDG) | from calibration curve 10 |
| Sodium dodecyl sulfate | 100 | □ | 0 | 21.76 | 18.75 |
| | | NaCl | 50 | 19.28 | 17.71 |
| | | | 100 | 14.96 | 15.90 |
| | | | 200 | 10.60 | 14.07 |
| | | | 400 | 7.40 | 12.72 |
| | | KCl | 50 | 18.24 | 17.27 |
| | | | 100 | 14.52 | 15.71 |

TABLE 10-continued

| Surfactant in aqueous sample | | Inorganic salt in aqueous sample | | Quantitative value (g) of phase-changing probe (2-EHDG) | Solution physical property index (corresponding HLB) from calibration curve 10 |
|---|---|---|---|---|---|
| Type | Concentration (mmol/kg) | Type | Concentration (mmol/kg) | | |
| | | | 200 | 9.96 | 13.80 |
| | | | 400 | 6.76 | 12.45 |
| | | CaCl$_2$ | 25 | 14.72 | 15.80 |
| | | | 50 | 8.08 | 13.01 |
| | | | 100 | 3.32 | 11.01 |
| | | | 150 | 3.12 | 10.93 |
| | | | 200 | 2.80 | 10.79 |
| | | | 400 | 2.36 | 10.61 |

The invention claimed is:

1. A method for estimating a hydrophobicity of an aqueous sample containing a surfactant and water, comprising:
adding an oil component and a phase-changing probe to the aqueous sample, and estimating the hydrophobicity of the aqueous sample from an amount of the phase-changing probe when a phase structure of the mixture changes;
wherein the phase-changing probe is a compound represented by the following general formula (1):

$$R^1\text{—O-}(AO)_n\text{—}R^2 \qquad (1)$$

wherein $R^1$ is a hydrocarbon group with 2 or more and 9 or less carbons; $R^2$ is a hydrogen atom or a hydrocarbon group with 1 or more and 20 or less carbons; A is an alkylene group with 2 or more and 3 or less carbons; and n is a number of 0 or more and 10 or less when $R^2$ is a hydrogen atom and a number of 1 or more and 10 or less when $R^2$ is a hydrocarbon group; and
wherein the surfactant is an anionic surfactant, a cationic surfactant, an amphoteric surfactant, or a nonionic surfactant that is selected from polyoxyalkylene alkyl ether of the following formula (2), polyoxyalkylene alkylaryl ether, polyoxyalkylene alkyl thioether, polyoxyalkylene alkylaryl thioether, polyoxyalkylene alkyl ester, polyoxyalkylene sorbitan monoalkyl ester, polyoxyalkylene alkylamine, polyoxyalkylene alkyl amide, alkyl glyceryl ether, saccharide ester and fatty acid ethanol amide, $$R^3\text{—O—}(BO)_m\text{—H} \qquad (2)$$

wherein $R^3$ is a hydrocarbon group with 10 or more and 20 or less carbons; B is an alkylene group with 2 or more and 3 or less carbons; and m is a number of 1 or more and 50 or less.

2. The method according to claim 1, wherein the hydrophobicity of the aqueous sample is estimated from a liquid physical property index of an HLB value.

3. The method according to claim 1, wherein the hydrophobicity of the aqueous sample is estimated from a liquid physical property index of an HLB value in a calibration curve prepared in the following manner:
<Preparation of the calibration curve>
to a precursor sample containing a surfactant with a known Griffin's HLB value and water, an oil component and amount that are the same as added to the aqueous sample is added to the precursor sample to prepare a standard sample,
the same phase-changing probe as the one added to the aqueous sample is added to the standard sample and an amount of the phase-changing probe is quantified when a phase structure of the standard sample changes,
this quantification is performed for a plurality of surfactants with different Griffin's HLB values under the same conditions to obtain a plurality of quantitative values,
at this time, the concentration of the surfactant with a known Griffin's HLB value in the precursor sample is the same as the concentration of the surfactant in the aqueous sample for which the amount of the phase-changing probe is measured, and compounds having different structures are used for the phase-changing probe agent and the surfactant with a known Griffin's HLB value, and
the calibration curve is prepared from the respective quantitative values and the HLB values of the surfactants included in the standard samples that provide the quantitative values.

4. A method for estimating a hydrophobicity of an aqueous sample containing a predetermined concentration of surfactant and water, comprising:
preparing a standard sample by adding an oil component and optionally a solvent to a precursor sample containing water and a surfactant with a known Griffin's HLB value, the concentration of the surfactant with a known Griffin's HLB value being the same as the concentration of the surfactant in the aqueous sample; adding to the standard sample a phase-changing probe consisting of a compound having a different structure than that of the surfactant with a known Griffin's HLB value to quantify an amount of the phase-changing probe required until a phase structure of the standard sample changes; performing this quantification for a plurality of surfactants with different Griffin's HLB values under the same conditions to obtain a plurality of quantitative values; and preparing a calibration curve from the quantitative values and the HLB values of the surfactants included in the standard samples that provide the quantitative values,
preparing a measurement sample by adding to the aqueous sample the same oil component and optional solvent as those added to the precursor sample in the same respective amounts as those in the precursor sample; adding to the measurement sample the same phase-changing probe as the one used for the measurement of the quantitative values of the calibration curve; and quantifying an amount of the phase-changing probe required until a phase structure of the measurement sample changes, and with values of the HLB value in the calibration curve defined as liquid physical property index of an HLB value, estimating the hydrophobicity of the aqueous sample from a liquid physical property index of an HLB value corresponding to a quantitative value of the phase-changing probe for the measurement sample; and wherein the phase-changing probe is a compound represented by the following general formula (1):

$$R^1\text{—}O\text{-}(AO)_n\text{—}R^2 \qquad (1)$$

wherein $R^1$ is a hydrocarbon group with 2 or more and 9 or less carbons; $R^2$ is a hydrogen atom or a hydrocarbon group with 1 or more and 20 or less carbons; A is an alkylene group with 2 or more and 3 or less carbons; and n is a number of 0 or more and 10 or less when $R^2$ is a hydrogen atom and a number of 1 or more and 10 or less when $R^2$ is a hydrocarbon group; and wherein the surfactant is an anionic surfactant, a cationic surfactant, an amphoteric surfactant, or a nonionic surfactant that is selected from polyoxyalkylene alkyl ether of the following formula (2), polyoxyalkylene alkylaryl ether, polyoxyalkylene alkyl thioether, polyoxyalkylene alkylaryl thioether, polyoxyalkylene alkyl ester, polyoxyalkylene sorbitan monoalkyl ester, polyoxyalkylene alkylamine, polyoxyalkylene alkyl amide, alkyl glyceryl ether, saccharide ester and fatty acid ethanol amide, $$R^3\text{—}O\text{—}(BO)_m\text{—}H \qquad (2)$$

wherein $R^3$ is a hydrocarbon group with 10 or more and 20 or less carbons; B is an alkylene group with 2 or more and 3 or less carbons; and m is a number of 1 or more and 50 or less.

5. The method according to claim 4, wherein the phase structure of the standard sample and/or measurement sample before adding the phase-changing probe comprises one or more structures selected from an oil phase (O phase), a reversed micellar oil solution phase (Om phase), a bicontinuous phase (D phase), a micellar solution phase (Wm phase) and a water phase (W phase).

6. The method according to claim 3, wherein the surfactant with a known Griffin's HLB value is a compound represented by the following general formula (2):

$$R^3\text{—}O\text{—}(BO)_m\text{—}H \qquad (2)$$

wherein $R^3$ is a hydrocarbon group with 10 or more and 20 or less carbons; B is an alkylene group with 2 or more and 3 or less carbons; and m is a number of 1 or more and 50 or less.

7. The method according to claim 1, wherein the oil component is a compound selected from hydrocarbons, ethers and esters, the compound having a solubility in water of 1 g/100 g or less at 25° C. and being liquid at 25° C.

8. The method according to claim 1, wherein the concentration of the surfactant in the aqueous sample is 1 mmol/kg or more and 500 mmol/kg or less.

9. A method for adjusting a hydrophobicity of an aqueous composition, comprising:
    estimating a hydrophobicity of an aqueous composition containing a surfactant and water by the method according to claim 1; and
    in response to the estimated hydrophobicity, changing the composition of the aqueous composition to adjust the hydrophobicity of the aqueous composition.

* * * * *